United States Patent [19]

Hall et al.

[11] Patent Number: 5,218,426
[45] Date of Patent: Jun. 8, 1993

[54] HIGHLY ACCURATE IN-SITU DETERMINATION OF THE REFRACTIVITY OF AN AMBIENT ATMOSPHERE

[75] Inventors: John L. Hall, Boulder, Colo.; Peter J. Martin, Encinitas, Calif.; Mark L. Eickhoff, Boulder, Colo.; Michael P. Winters, Pasadena, Calif.

[73] Assignee: The United States of America as represented by the Secretary of Commerce, Washington, D.C.

[21] Appl. No.: 723,950

[22] Filed: Jul. 1, 1991

[51] Int. Cl.[5] .............................................. G01B 9/02
[52] U.S. Cl. .................................... 356/361; 356/352
[58] Field of Search .............................. 356/361, 352

[56] References Cited

U.S. PATENT DOCUMENTS

| | | |
|---|---|---|
| 3,614,236 | 10/1971 | Steinemann et al. |
| 4,329,058 | 5/1982 | James et al. .................... 356/361 |
| 4,455,089 | 6/1984 | Yeung et al. .................... 356/361 |
| 4,553,841 | 11/1985 | Coppa et al. .................... 356/361 |
| 4,690,562 | 9/1987 | Davies et al. ................... 356/361 |
| 4,743,114 | 5/1988 | Crane ............................. 356/352 |

OTHER PUBLICATIONS

Byer et al. "A Wavelength Meter", Laser Spectroscopy III, pp. 414-415 (1977).
Fischer et al., "Computer Controlled Fabry-Perot Wave Meter", Optics Communications, vol. 39, No. 5, pp. 277-282 (1981).
Hays, "Circle to line interferometer optical system", Applied Optics, vol. 29, No. 10, pp. 1482-1489 (Apr. 1990).
Anderson et al., "Compressible Fabry-Perot refractometer", Applied Optics, vol. 26, No. 22, pp. 4835-4840 (Nov. 1987).

*Primary Examiner*—Samuel A. Turner
*Attorney, Agent, or Firm*—Harold A. Burdick

[57] ABSTRACT

A highly accurate in-situ determination of the refractivity of an ambient atmosphere is disclosed, which determination is utilizable to enhance the accuracy of a quantity measurement. The system includes use of a refractometer exposed to an ambient atmosphere and having light directed thereto to form an optical interference fringe pattern having a dependence upon the refractivity of the ambient atmosphere. The fringe pattern is measured as a function of angle either by sequentially scanning a collimated input beam in angle while collecting and detecting the transmitted light, or by imaging (onto a multi-element detector) the angular exit space of the interferometer illuminated with a diverging input beam. The electrical output of the detector is processed to provide an output indicative of the index of refraction of the ambient atmosphere. The determined index of refraction is utilizable to enhance the accuracy of a quantity measurement, such as, for example, the distance measurement provided by a Fabry-Perot or displacement-measuring Michelson interferometer.

25 Claims, 4 Drawing Sheets

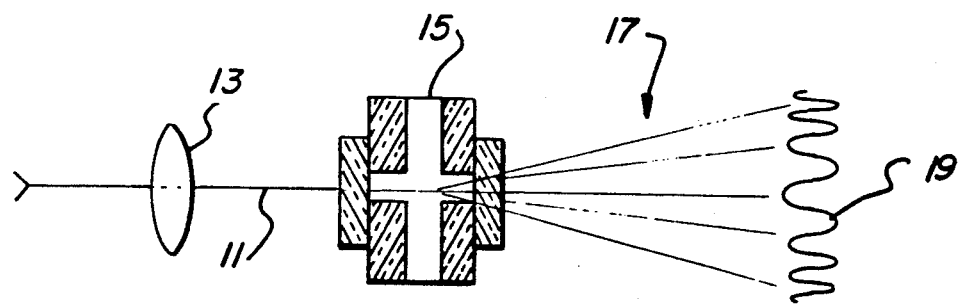
Fig_1
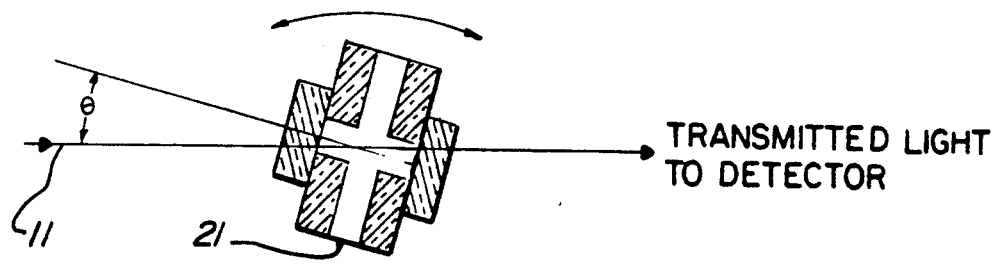
Fig_2A
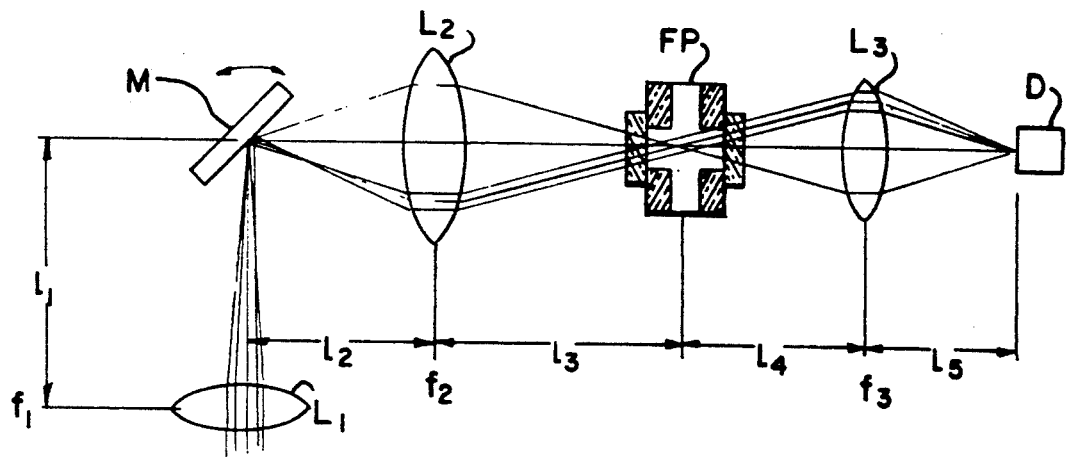
Fig_2B

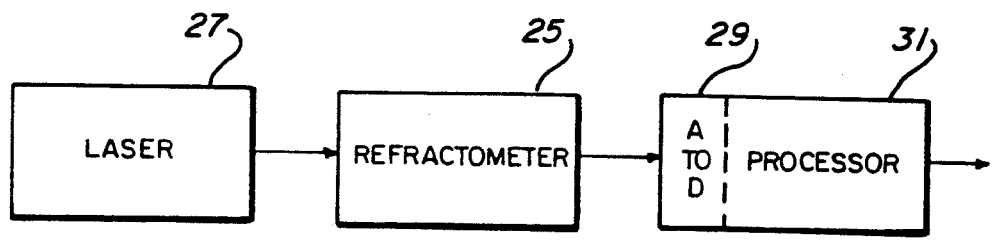
Fig_3
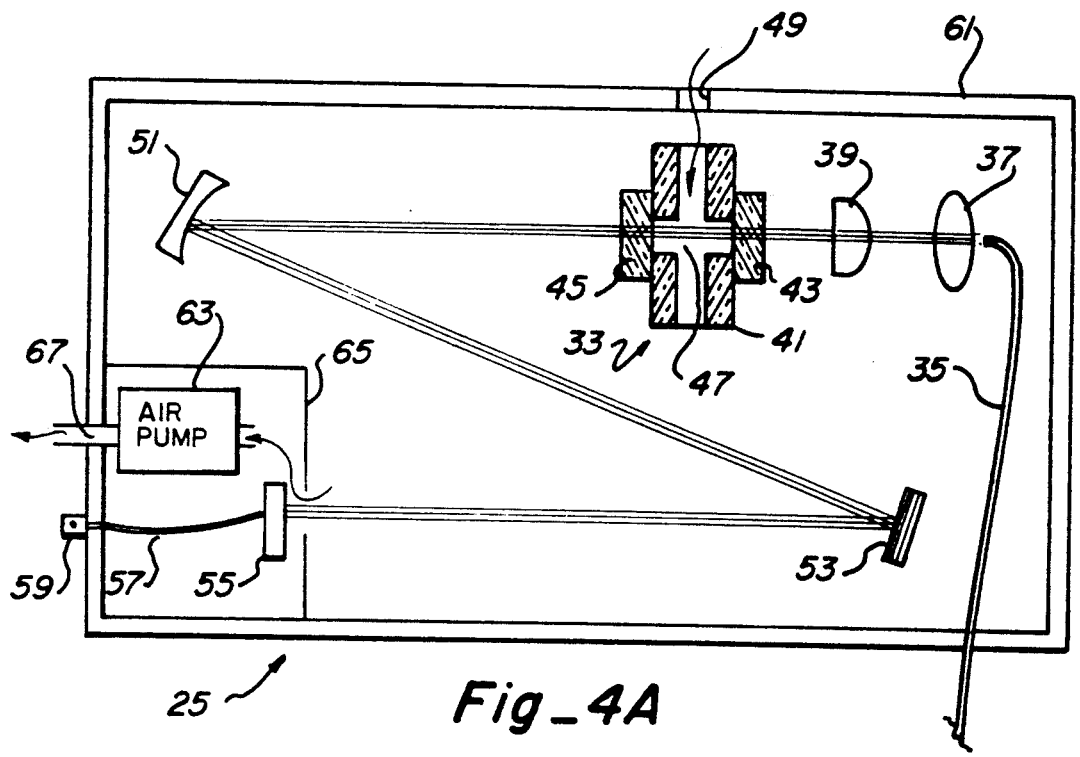
Fig_4A
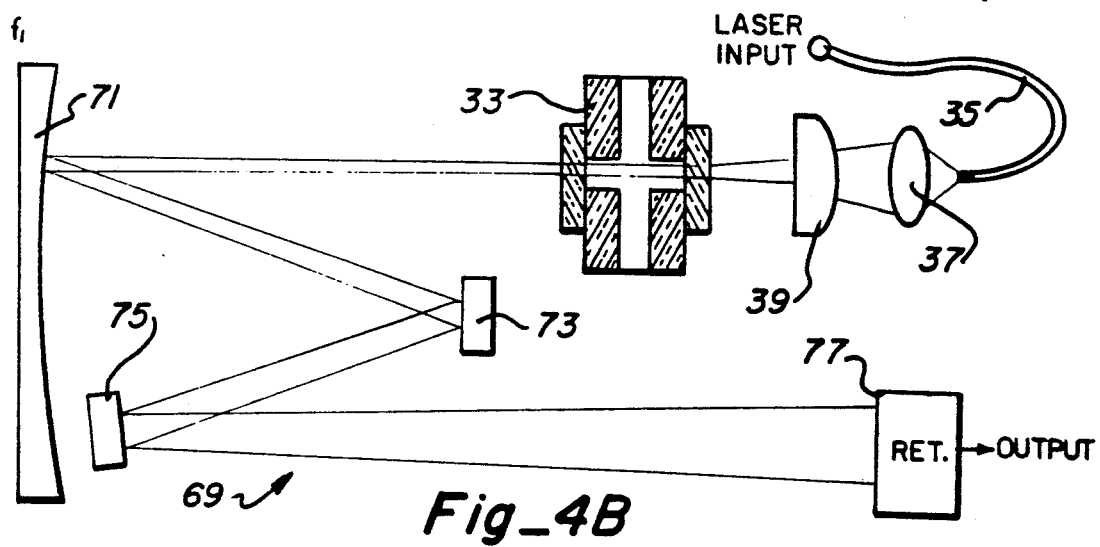
Fig_4B

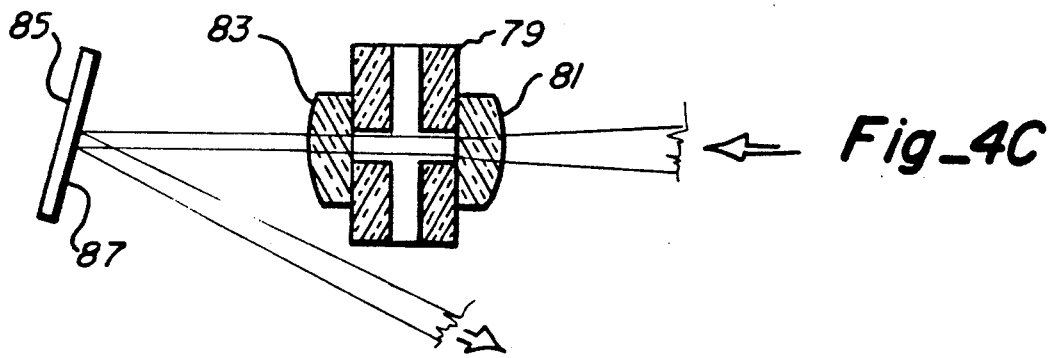

Fig_4C

```
DATA ACQUISITION: A/D CONVERTER PLACES
DIGITIZED FRINGE PATTERN INTO MEMORY FOR
PROCESSING. FRINGE PATTERN IS READ 5 OR 10
TIMES AND THEN AVERAGED.
```
↓
```
PEAK-FINDING "FILTER": CONVOLUTE DATA
WITH STEP/ANTISTEP FUNCTION (1st DERIVATIVE)
AND LOOK FOR ZERO CROSSINGS.
```
↓
```
NONLINEAR LEAST SQUARES FIT FOR
PARAMETERS EXCESS ORDER AND SYMMETRY
CENTER.
```
↓
```
USE THE CENTER TO "LINEARIZE" THE DATA:
TRANSFORM TO A NEW AXIS WHERE PEAKS
APPEAR EVENLY SPACED AND SYMMETRIC.
```
↓
```
PEAK-FINDING "FILTER": CONVOLUTE DATA
WITH STEP/ANTISTEP FUNCTION (1st DERIVATIVE)
AND LOOK FOR ZERO CROSSINGS.
```
↓
```
LINEAR LEAST SQUARES FIT THE DATA FOR
EXCESS ORDER ON LEFT AND EXCESS ORDER
ON RIGHT. OUTPUT THE AVERAGE OF THESE.
```

Fig_5

Fig_6A
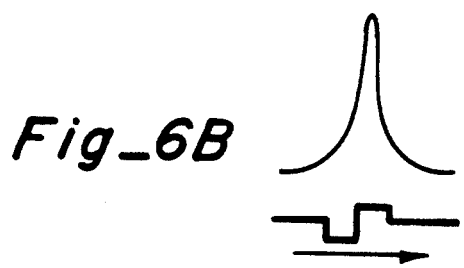
Fig_6B
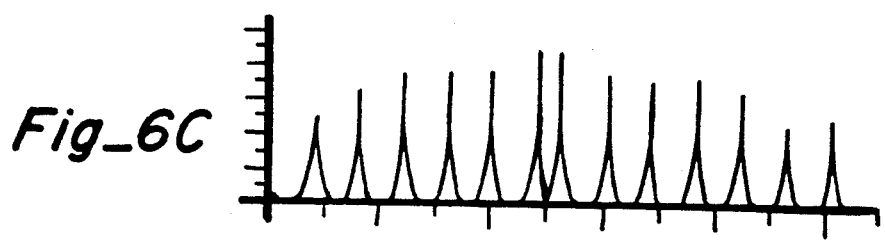
Fig_6C
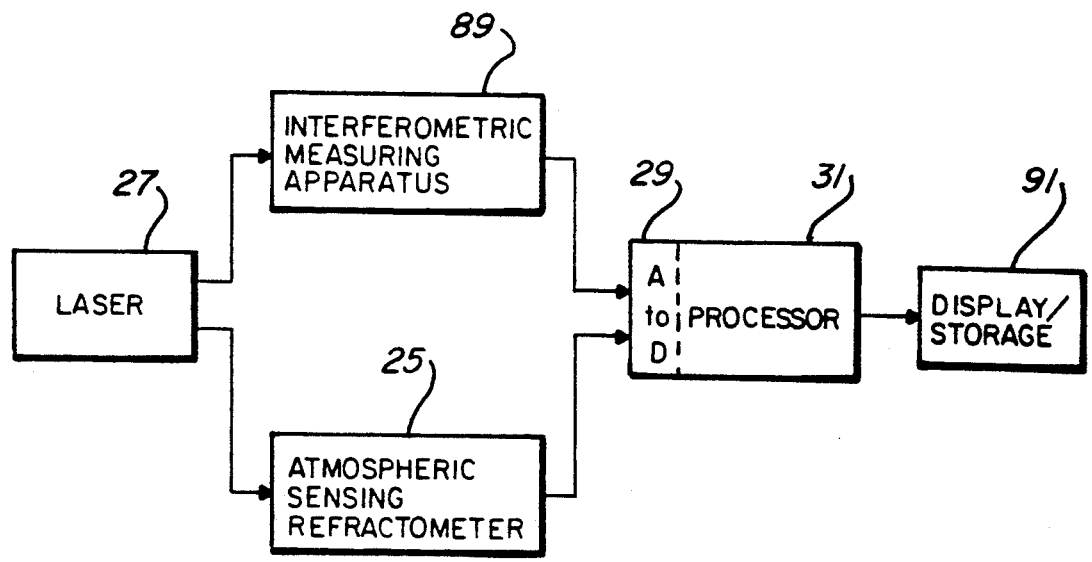
Fig_7

HIGHLY ACCURATE IN-SITU DETERMINATION OF THE REFRACTIVITY OF AN AMBIENT ATMOSPHERE

FIELD OF THE INVENTION

This invention relates to refractivity determination, and, more particularly, relates to in-situ determination of the refractivity of an ambient atmosphere and use thereof.

BACKGROUND OF THE INVENTION

Over time, it has become increasingly useful and necessary to enhance the accuracy of the measurement of a quantity, such as, for example, distance.

Interferometry now provides a convenient and highly sensitive method for measuring a quantity, such as distance, optically. For some applications, such as, for example, those which relate a common distance measured by two radiations of differing wavelength, it may be optimally effective to make the measurements in vacuum to obtain a wavelength ratio as accurately as possible. For other measurement situations, however, where, for example, the objective is to establish a physical distance, it is clearly more attractive to measure the distance in the ambient atmosphere rather than in vacuum.

Apparatus is commercially available offering intrinsic fringe-counting measurement capability in vacuum with inaccuracies in the range of one part in $10^8$. To achieve such accuracy in an ambient atmosphere, such as, for example, in the attractive case of interferometry in air, the measured length would have to be corrected for the refractive index of the atmosphere, a factor somewhat greater than unity, and dependent upon the gaseous composition, temperature, pressure, humidity, and the like.

In years of careful work, B. Edlen developed an empirical expression for the index of refraction (B. Edlen, "The Refractive Index of Air", Metrologia 2, 71–80 (1966)) based upon data of H. Barrell and J.E. Sears Jr. (Philosophical Transactions of the Royal Society of London, Series A, 238 p. 1 (1939)). Many others have extended this analysis to better represent the density dependence using local field corrections and virial expansions, for example. More recently, an international collaboration of experts has recommended the following approximate formula for the index of refraction (n) of standard air near usual laboratory conditions:

$$n - 1 = \frac{D(0.104127 \times 10^{-4})P}{1 + 0.3671 \times 10^{-2}T} - 0.42063 \times 10^{-9}F,$$

with $D = 0.27651756 \times 10^{-3}[1 + 54 \times 10^{-8}(C - 300)]$, where P is the pressure in Pa, T is the temperature in degrees centigrade, F is the partial pressure of water vapor in Pa, and C is the $CO_2$ concentration in ppm. The formula set forth above represents the index of refraction at the wavelength of the 633 nm HeNe laser (632.991 398 nm in vacuum).

It can be seen that the correction due to atmospheric refractivity amounts to 270 parts per million at sea level. Thus, to reach an inaccuracy of 1 part in $10^8$, it is necessary to know the refractivity at the level of 1 part in 27,000. One way to reduce this sensitivity is to employ a balanced-path interferometer. For many applications, however, it is necessary, or at least more desirable, to measure through an unbalanced distance interval of about one meter due to several technical reasons. Furthermore, making the apparatus single-ended allows the heat-generating laser apparatus to be located somewhat away from the sensitive area where it is desired to make the actual measurement. The result is that the interferometric length measurement accuracy is often unacceptably compromised by inaccurate knowledge of the atmospheric index of refraction.

One possibility for the in-situ determination of the atmospheric index of refraction would be to individually measure (or estimate) the atmospheric pressure, temperature, humidity, and $CO_2$ content. A measurement objective of even 0.1 ppm relative length accuracy, however, requires pressure and temperature measurement at the 0.02% level, viz. 0.2 millibar and 0.06 K. These values are several orders of magnitude beyond any practical known calibration of generic transducers and so must be obtained by painstakingly careful and expensive calibration relative to accurate working standards. Furthermore, the refractivity of water vapor is about 15% below that of dry air, so the relative humidity must be known to within 0.14% of absolute, which is not easy to achieve without direct measurement of the dew point. Finally, the environmental atmosphere is enriched beyond the usual 300 ppm level of $CO_2$ concentration by the respiration of people working in the measurement area. A factor of 2 increase in the $CO_2$ concentration is typical for a few hours work in a closed room. However, the refractivity of $CO_2$ is approximately equal to (somewhat greater than) that of standard air so that changes in its concentration are only marginally significant at the $1:10^7$ level.

Prior art devices have addressed problems related to index of refraction measurements, but not for the purpose of quantifying the index of refraction of the surrounding atmosphere. For example, the use of Fabry-Perot etalons in vacuum to determine wavelength either with vidicon readout and analog processing (R.L. Byer, J. Paul and M.D. Duncan, "A Wavelength Meter", Laser Spectroscopy III, page 414 (1977)) or solid state detectors and digital processing (A. Fischer, R. Kullmer and W. Demtroder, "Computer Controlled Fabry-Perot Wavemeter", Optics Communications, 39, 277–282 (1981)) has heretofore been suggested. In addition, a technique for mapping a significant fraction of each Fabry-Perot ring into a corresponding spot (with an inherent loss of accuracy) has also been suggested (Hays, "Circle to Line Interferometer Optical System", Applied Optics, 29, 1482–1489 (1990)). The slight compression of Fabry-Perot etalons due to increases in atmospheric pressure has also been observed (M. Andersson, L. Eliasson and L.R. Pendrill, "Compressible Fabry-Perot Refractometer", Applied Optics, 26, 4835–4840 (1987)).

Previous patents also address related problems. U.S. Pat. No. 3,614,236 shows use of changes in the direction of the illumination of a Fabry-Perot interferometer caused by changes in atmospheric refractivity, to cancel changes in the interference condition caused by atmospheric pressure changes within the interferometer, with the apparatus including a HeNe laser and a plurality of optical units and detectors to count fringes. U.S. Pat. No. 4,329,058 shows a fiber optic sensor based on Fabry-Perot interferometry, and shows use of a plurality of charge coupled devices and a microprocessor having a decoding algorithm, with the device providing a means for measuring physical parameters at remote locations.

Thus, there is a need for a simple, robust system and method for determining the index of refraction of an ambient atmosphere, such as air, during the quantity measurement (such as measurement of distance, or length), for example, during the "step and repeat" process of patterning integrated circuit wafers using photolithography. As this industry moves toward tracewidths far below 1 μm, it will become necessary to be able to determine the index of refraction even better, toward the 1:10$^8$ level.

SUMMARY OF THE INVENTION

This invention provides a system and method for making an accurate in-situ determination of the refractivity of an ambient atmosphere. In addition, the determined index of refraction is utilizable to enhance the accuracy of a quantity measurement such as distance.

A refractometer exposed to an ambient atmosphere has light directed thereto to form an optical interference pattern that is dependent upon the refractivity of the ambient atmosphere. The angular dependence of the interference pattern is relied upon for readout of refractivity information. The fringe pattern is measured as a function of angle either by sequentially scanning the collimated input beam in angle, while collecting and detecting all of the transmitted light, or by imaging the angular exit space of the interferometer in the far field onto a multi-element detector. The electrical output of the detector is processed to provide an output indicative of the index of refraction of the ambient atmosphere. The determined index of refraction is utilizable to enhance the accuracy of a quantity measurement such as, for example, the distance interval provided by a Fabry-Perot or displacement-measuring Michelson interferometer.

It is therefore an object of this invention to provide a system and method for providing an accurate in-situ determination of the refractivity of an ambient atmosphere.

It is another object of this invention to provide a system and method for making an in-situ determination of the index of refraction of an ambient atmosphere and utilizing the same to enhance the accuracy of a quantity measurement.

It is still another object of this invention to provide an improved system and method for enabling in-situ determination of the refractivity of an ambient atmosphere through use of a refractometer exposed to the ambient atmosphere and receiving light to form an optical interference fringe pattern that is used to determine the index of refraction of the ambient atmosphere.

It is another object of this invention to provide an improved system and method for enabling in-situ determination of the refractivity of an ambient atmosphere through use of a refractometer exposed to the ambient atmosphere and receiving light to form an optical interference fringe pattern and measuring the fringe pattern as a function of angle either by measurement of the collimated input beam in angle or by imaging the angular exit space of the interferometer in the far field onto a detector.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate principles of the invention and complete embodiments of the invention according to the best mode so far devised for the practical application of the principles thereof, and in which:

FIG. 1 is an optical flow sketch illustrating the principle of operation enabling simultaneous readout of an entire interference pattern utilizing an interferometer;

FIG. 2A is a partial flow sketch illustrating the principle of operation of a tiltable interferometer to enable sequential angular scanning of a collimated input beam;

FIG. 2B is an optical flow sketch illustrating utilization of a galvanometer-mounted mirror to enable sequential readout of an angularly scanned collimated input beam;

FIG. 3 is a block diagram illustrating the system of this invention;

FIG. 4A is an optical flow sketch illustrating the refractometer shown in block form in FIG. 3;

FIG. 4B is an optical flow sketch illustrating an alternate embodiment of the refractometer shown in block form in FIG. 3;

FIG. 4C is a partial flow sketch illustrating an alternate embodiment of the configuration for the interferometer and focusing mirror shown in FIGS. 4A and 4B;

FIG. 5 is a flow chart of the algorithm used in the processor shown in block form in FIG. 3;

FIGS. 6A, 6B and 6C provide a series of typical waveforms illustrating the flow chart of FIG. 5; and FIG. 7 is a block diagram illustrating use of the system as shown in FIG. 3 in connection with an interferometer used to measure a predetermined quantity.

DESCRIPTION OF THE INVENTION

When the ambient atmosphere is a fluid, such as air, the index of refraction shortens the wavelength of light in that atmosphere compared to the wavelength of that same light in a vacuum. In this invention, the air wavelength of laser light is measured and compared with the known vacuum wavelength to determine the index of refraction. The air wavelength is measured by determining the number of half-wavelengths, or orders, within a well-known mechanical length given by a rigid spacer, or etalon. If the etalon length is denoted by L, the laser frequency by $\nu$, and the index of refraction by n, then the following relation exists:

$$N = \left[ \frac{\nu}{c/2L} \right] n,$$

where c is the speed of light in vacuum, and N is the total order number. The bracketed portion of the above relation is the order number in a vacuum, ($N_{vac}$) of a Fabry-Perot interferometer formed by attaching mirrors to the etalon. That order number is a determinable calibration constant. By an appropriate choice of L, rather imprecise information about the pressure and temperature of the ambient atmosphere can fix the integer part of N for the particular measurement conditions of interest. The fractional part of N is determined by detailed examination of the visible fringe pattern carried out by a computer program, or fringe fitting algorithm.

This invention provides a powerful yet simple noninvasive system and method for determining in-situ the refractivity of an ambient atmosphere. Angle-scanning is utilized, and the principle of operation of angle-scanning using a Fabry-Perot refractometer (etalon) is illustrated in FIG. 1. As illustrated, an input beam 11 of concentrated diverging light from lens 13 is coupled to refractometer 15. Divergent light 17 from refractometer 15, having a typical pattern 19, is applied to suitable optics and a multi-element detector, which detector simultaneously reads the entire interference pattern with the fringe interference phase being determined from the angular pattern.

Sequential readout is illustrated by the principle of operation illustrated in FIG. 2A using a tiltable etalon 21 receiving collimated beam 11. The etalon transmission is measured directly as a function of angle ($\theta$) by varying the direction of the collimated optical input beam relative to the axis of the etalon. The interference phase is determined from the angular distribution of Fabry-Perot resonances. The output data is processed to obtain the index of refraction (n) using:

$$T(\theta) = \frac{1}{1 + F^2 \sin^2\left[\frac{2nL \cos \theta}{\lambda o}\right]}$$

where F is $2/\pi \times$ finesse, L is thickness of etalon, $\theta$ is incidence angle, and $\lambda o$ is the vacuum wavelength of the incident light.

A system for enabling sequential readout using angle scanning of the input beam is illustrated in FIG. 2B. As shown, the collimated light beam 11 from lens $L_1$ (having focal length $f_1$) is directed to galvanometer-mounted turning mirror M (with a distance $l_1$ therebetween). Mirror M steers the input beam direction in a precisely controllable manner. Lens $L_2$ (at a distance $l_2$ from mirror M and having a focal length $f_2$) recollimates the input beam with a magnified diameter, and reimages the rotation point of the mirror into the center of interferometer FP (Lens $L_2$ is at a distance $l_3$ from the center of interferometer FP). The recollimation condition (adjustment of lens $L_1$ and $L_2$) is dependent upon $l_1 + l_2 = f_1 + f_2$, while re-imaging of the "impact" point on the galvo-mirror (adjustment of lens $L_2$) is dependent upon $$\frac{1}{l_2} + \frac{1}{l_3} = \frac{1}{f_2}.$$

This galvo-mirror rotation leads to an angular scan of the transmission function of interferometer FP. All of the transmitted light from interferometer FP at a given angle is coupled to detector D by lens $L_3$. (Lens $L_3$ has a focus $f_3$, is at a distance $l_4$ from interferometer FP, and is at a distance $l_5$ from detector D). Re-imaging of the interferometer center onto the detector (adjustment of lens $L_3$) is dependent upon $$\frac{1}{l_4} + \frac{1}{l_5} = \frac{1}{f_3}.$$

Under this condition, all of the transmitted light is incident upon the detector independent of $\theta$. After digitization of data, processing is equivalent to that described hereinafter with respect to processing of the fringe pattern obtained by imaging the angular exit space of the interferometer in the far field upon a multi-element detector.

As shown in FIG. 3, system 23 includes a refractometer 25 that is adapted to receive light, preferably from a laser source 27. Refractometer 25 provides an electrical output signal that is derived from an interference fringe pattern, as brought out more fully hereinafter, and the electrical output signal is coupled to analog-to-digital converter 29 (shown as a part of processor 31). Processor 31 is preferably a microprocessor utilizing a fringe fitting algorithm, with the processor providing an output indicative of the index of refraction of the ambient atmosphere.

The presently preferred embodiment of refractometer 25 is illustrated by FIG. 4A. As shown, light, as from source 27 (preferably provided by a frequency-stabilized laser source such as a frequency-stabilized HeNe laser), is adapted to be coupled as concentrated diverging light to plane-plane Fabry-Perot etalon (interferometer) 33 through optical fiber 35, spherical lens 37 and cylindrical lens 39. Because of the input wavefront divergence, a ring-shaped interference pattern is realized, with the first ten or twelve fringes illuminated on either side of center. By employing cylindrical expansion of the input beam, only a limited diametral zone of the fringe rings is illuminated, thus conserving the available light.

Fabry-Perot interferometer 33 includes an etalon 41 to which two flat mirrors 43 and 45 are optically contacted. Etalon 41 is preferably a solid piece of Zerodur M or ULE (for good thermal and mechanical stability) machined and polished to have flat and parallel endfaces. The center is drilled out to form an open interaction (sampling) region 47. A sampling vent 49 allows the ambient atmosphere into the interaction region 47.

A concave focussing mirror 51 focuses the developed interference fringe pattern by way of mirror 53 onto a multi-element detector 55. Concave mirror 51 serves to map the fringes into the far field, and flat mirror 53 folds the optical path so that the refractometer design may be compact. The electrical output signals developed by detector 55 are coupled through lead 57 to output connector 59 (for conducting the output signals to A/D unit 29 of processor 31.

Refractometer 25 is preferably enclosed in chamber 61. Sampling inlet 49 allows an ambient atmosphere, such as air, into the chamber so that interferometer 33 is exposed to the ambient atmosphere. Air pump 63, preferably partially isolated by walls 65 as indicated in FIG. 4A, is utilized to induce circulation of the ambient atmosphere within chamber 61, particularly by drawing air in through Fabry-Perot interferometer 33 and using the air pump to exhaust the heat generated by the multi-element detector (also partially isolated by walls 65) through outlet 67 adjacent to air pump 63.

An alternate embodiment 69 of the refractometer is illustrated by FIG. 4B. As shown, optical fiber 35, spherical lens 37 and cylindrical lens 39 are used to couple light from laser source 27 to Fabry-Perot etalon 33, which etalon may be identical to the etalon shown in FIG. 4A. As also shown in FIG. 4B, the interference fringe pattern is formed by focusing mirror 71 and mirrors 73 and 75 onto multi-element detector 77.

When the ambient atmosphere is a fluid, such as air, the constancy of the vacuum wavelength of the stabilized laser allows measurements of the optical length of the etalon to be interpreted as measurements of the effective air wavelength of the laser. The relation above set forth for N is utilized. For example, consider the case of $\nu = 473$ THz (the usual $\nu = 633$ nm HeNe line), $L = 3.17$ cm. Then $N_{vac} = 10^5$, and the extra number of fringes due to the air is 27. With a 1% pressure measurement order determination is unambiguous because the uncertainty would be only 0.27 fringes. Similarly, with a 1K temperature measurement uncertainty, an uncertainty exists of only 0.1 fringes (these uncertainties evidently pertain to the contribution due to the atmospheric index of refraction). Thus, physical measurements of modest precision allow determination of the interference order number.

Additional changes could be produced by the environmental effects acting on the etalon itself. For example, using Zerodur or ULE as spacer elements, a direct thermal expansion coefficient of $\sim 5 \times 10^{-8}$ per degree K is expected. With $10^5$ fringes, the direct effect of thermal expansion is only 5 millifringes for a 1K change. This can be taken into account in the calibration/readout algorithm, but is otherwise innocuous.

There is, however, a marginally important effect from the direct pressure action to compress the interferometer spacer's length. It is expected that the effect will scale as $\delta L/L \approx -P/3B$, where B is the bulk modulus (the bulk modulus $B = Y/(3(1-2\mu))$, where Y is Young's modulus and $\mu$ is the Poisson ratio). Again taking rough numericals for Zerodur ($Y \sim 91 \times 10^3$ N/mm$^2$ $\mu = 0.24$, so $B = 58.3 \times 10^3$ N/mm$^2$), there is a compression of 0.060 fringes from vacuum to atmospheric pressure. This appears as a scale correction of $-2.2$ parts/thousand for the pressure-induced changes. Again, knowing the pressure to 1% makes the uncertainty in this effect below the $10^{-8}$ level. Of course, the fringes themselves form a better pressure readout, so the correction can be made very precisely by use of determined calibration data.

The long-term change of the Zerodur etalon with time is very slow—below $10^{-7}$ per year for Zerodur and 10-fold less for ULE—and has a highly predictable gradient. Thus, knowledge of the date of annealing, taken with the date of the measurement of interest, serves to define the length change to within a few parts in $10^9$ for several years without recalibration.

As brought out above, the far field pattern of the interferometer is detected by a multi-element photodetector array. The detector may include a plurality of charge coupled device (CCD) photosites (as indicated in FIG. 4A), or a plurality of photodiodes as in a Reticon (as indicated in FIG. 4B). In either case, the detector produces a staircase electrical waveform (of length 1024, for example) representing the average light level at many, very precisely-located detector/sample points. This waveform, which has high intrinsic signal/noise ratio, is converted to digital form and further enhanced by multi-scan averaging carried out at processor 31.

A computer algorithm is utilized in processor 31 (preferably a micro-computer) which extracts the physical information contained in the digital waveform. The locations of the peaks within the waveform, representing the angles of bright interference fringes, determine the symmetry center and the fractional fringe phase. The latter quantity is the physical parameter of interest for the determination of the index of refraction. It has been found both in simulation and experiment that the fringe phase may be determined with an uncertainty of approximately $2 \times 10^{-4}$ orders for the signal to noise ratios which are available. A fast and powerful linearization and fitting algorithm, developed by M.P. Winters and based on the use of a fringe center-finding idea (J.J. Snyder, Applied Optics, 19, 1223 (1980) is explained in greater detail hereafter.

Since the accuracy of the fitting algorithm limits the accuracy of the index of refraction determination, possible systematic errors in the fit are examined in detail. With simulation, it has been found that shifts of several units of $10^{-4}$ orders can be produced by a systematic pulling of the fringes toward the center of the illumination envelope. A variety of correction schemes can be utilized including: 1) FFT, bandpass filtering in the transform plane, followed by inverse FFT prior to fitting; 2) estimation of the envelope function by spline fits through the peaks and minima of the fringes, followed by normalization of the data prior to fitting; 3) analytic a posteriori correction of the output parameters using the envelope parameter estimates; or 4) full nonlinear least-squares fit including both envelope and fringe functions. It should be noted that a full nonlinear least-squares fit would recover several other physical parameters of interest including the amplitude, a possible DC offset, the sharpness of the fringes (finesse), and a scale factor concerning the overall size of the image.

It has been proven experimentally that the correct fringe fraction has been obtained. To so prove, light from a tunable dye laser was fed into the interferometer input optics alternately with light from the HeNe red reference laser. This alternation allows monitoring for drifts of the system or, more likely, the environmental conditions. The dye laser is locked to a reference/control cavity with 250 MHz free spectral range, only about 1/20 of the fsr of the Fabry-Perot unit utilized in this invention. Thus, by locking on successive orders of the laser's control cavity, $\sim 20$ points per Fabry-Perot order were obtained. As the shape of the ring fringes evolves continuously with phase, these twenty measurement points give a clear insight into possible unsuspected systematic fitting errors. An additional fine frequency scan capability is available based on the frequency offset produced with an acousto-optic modulator, driven by a frequency synthesizer.

The dye laser wavelength may be determined using a LambdaMeter with an imprecision below $10^{-8}$ (the JILA LambdaMeter, for example, now operates in the $< 10^{-9}$ domain). Operation is straight-forward, and the capability of the LambdaMeter forms the basis for precise calibration of the Fabry-Perot interferometer spacing, L. The method is essentially equivalent to the "method of exact fractions" used in classical interferometry with fixed-wavelength light sources.

Basically, measurement with the LambdaMeter of the dye laser wavelength corresponds to some observable reference phase in the Fabry-Perot unit. Tuning the dye laser 4.7 GHz in the example set forth provides the next order of interference. The LambdaMeter may be read to 10 MHz in a moment, and this indicates that the 4.7 GHz interval is known within approximately 1/300 of its value. The difference in the order numbers is still unambiguous if the laser frequency is changed a larger amount, say 50 orders, i.e., 325 GHz, or about 3 Å. The uncertainty would then be about 1/6 order. Taking the nearest integer, the fsr would be refined to $6 \cdot 10^{-5}$, or 0.28 MHz. Changing the laser frequency again, this time by 11.75 THz (150 Å), increases by another 50-fold the difference in the fringe numbers and leads to a knowledge of the etalon fsr at the level of $1.2 \cdot 10^{-6}$. The 10

MHz absolute uncertainty of the optical frequency makes a basically negligible contribution at this point, so that the integer order number can be unambiguously determined from $N = \nu/(fsr)$.

The fractional part of the ratio is contributed by two sources, a possible phase-shift-on-reflection associated with the mirrors and, of course by genuine measurement offsets. By using a source of known wavelength, such as the stable HeNe laser which has been heterodyne-calibrated relative to an $I_2$ stabilized laser, the mirror phase shift may be determined relative to the above-determined (or a standard assumed) integer order number.

It may be noticed that drift of the mirror phase shift is indistinguishable from an indicated change in the atmospheric index of refraction. Several techniques can ameliorate this situation. It would be possible, for example, to package the instrument so that a vacuum may be pulled on it. Indeed, periodic measurements of the zero-pressure fringe phase would serve to monitor the long-term drift of the Fabry-Perot spacer and of the mirror reflection phase shifts. Information from literature about mirror phase shifts and their aging suggests that overcoated Al may be preferable to usual dielectric mirrors because of humidity-sensitivity of the latter. Newer sputter-coating techniques may, however, solve this problem for dielectric mirrors.

In this described refractometer, alternate readout schemes may be utilized, including, for example, angle-scanning of the Fabry-Perot rings (using a galvanometer-deflected beam in the entrance optics).

FIG. 4C illustrates that an interferometer 79 having curved mirrors 81 and 83 could also be utilized in lieu of interferometer 33 as shown in FIGS. 4A and 4B. When interferometer 79 is used, then mirror 85 with a flat face 87 can be utilized in lieu of focussing mirrors 51 and 71 as shown in FIGS. 4A and 4B, respectively.

The algorithm preferably used by processor 31 is illustrated by the flow chart of FIG. 5, with typical illustrative waveforms being set forth in FIGS. 6A, 6B and 6C.

The algorithm is designed to find the excess, or fractional, order at the center of a digitized Fabry-Perot interference pattern, given the integer order of the etalon. The routine is designed to run as fast as possible while maintaining high accuracy in the calculations.

For data acquisition, the routine makes several calls to a compiled driver program and these calls specify how the analog data is to be digitized and stored. Direct memory access is utilized to give high data throughput (about 80 KHz). The analog video signal (as indicated in FIG. 6A) from the line image sensor (detector 55) is digitized 5 or 10 times and the results averaged to increase the signal-to-noise ratio. That averaged signal is normalized and stored in an array of 1024 elements.

Most of the information in the interference pattern is contained in the location of the peaks. The peak-finding subroutine is a fast digital filter. The data is convolved with a unit height step/anti-step function (as indicated in FIG. 6B). The convolution crosses zero when the filter passes over a peak. Monitoring the convolution as a function of filter position and looking for zero-crossings yields accurate locations of the peaks.

This information is then fit via a nonlinear least squares procedure in which the fit parameters are fractional order and center channel of the interference pattern. This method is inherently limited in accuracy—its ability to find the fractional order depends on how well it knows in advance the focal length of mirror 51 (FIG. 4A), 71 (FIG. 4B) or lens surface 83 (FIG. 4C). It can, however, determine the center channel of the pattern very accurately and that information is used in linearization of the fringe data (see FIG. 5).

For linearization of the pattern, the algorithm transforms the array from what it looks like in linear space to what it would look like in angular space before the focusing mirror. The advantages are that this space is independent of the focal length and the fringe peaks appear symmetric and evenly spaced. The algorithm builds a picture of the angular interference pattern by interpolating new data points from the old along an axis in angular space. A cubic spline interpolation is used which ensures that the new pattern will be continuous through the second derivative.

With the peaks symmetric and evenly spaced (as indicated typically in FIG. 6C), the algorithm uses the well-known, reliable technique of linear regression for least-squares fit. After a call to the peak-finding digital filter in the angular space, the algorithm fits the peak centers on each side of the fringe pattern to a straight line. Fitting each side independently and then averaging the two results compensates for any small error in the previously found center channel.

The algorithm further gives an estimate of the uncertainty in the calculated fractional fringe phase. Generally, uncertainties in parameters of a model are calculated based on the measurement errors in the raw data. But this is difficult with respect to the system and method of this invention. Instead, the linear least squares routine assumes a good fit and calculates uncertainties in its parameters based on the Chi-squared merit function evaluated with the current parameters. Also, the algorithm produces a graph of the linear least squares fit residuals, which can reveal systematic or imaging errors in the refractometer. Such information could be used to further refine the accuracy of the determination of the index of refraction.

The algorithm has been tested by numerically simulating interference patterns with known amounts of noise. These patterns, created with known fractional order and center channel, were then given to the algorithm and the values found were compared with the original values. With such testing, it has been found that the algorithm can find the fractional order to an accuracy of about 2 parts in $10^4$.

FIG. 7 illustrates the use of the system of this invention in conjunction with a measuring apparatus 89 (preferably an interferometric measuring apparatus). Such an apparatus can be, for example, a Michelson interferometer used to measure distance. When so utilized, the accuracy is enhanced by using the index of refraction of the ambient atmosphere (which is determined in-situ while the distance measurement is being made) to correct the distance measured by measuring apparatus 89. The output from the processor thus provides a highly accurate indication of the measured quantity (i.e., distance, for example) which can be displayed or stored with unit 91.

As can be appreciated from the foregoing, this invention provides a system and method for determining in-situ, the refractivity of an ambient atmosphere and use of the same to enhance the accuracy of a quantity measurement.

What is claimed is:

1. A system for accurate in-situ determination of the refractivity of an ambient atmosphere, said system comprising:
   light conducting means adapted to provide concentrated light from a frequency-stabilized light source;
   sampling means adapted to provide an ambient atmosphere the refractivity of which is to be determined;
   refractometer means exposed to said ambient atmosphere provided by said sampling means, said refractometer means receiving said concentrated light from said light conducting means;
   enabling means for causing said refractometer means to receive said concentrated light at different angles whereby said refractometer means, upon receipt of said concentrated light from said light conducting means, provides an optical interference fringe pattern which is dependent upon the refractivity of said ambient atmosphere;
   detector means for receiving said refractivity-dependent optical interference fringe pattern from said refractometer means, said detector means being sensitive to said refractivity-dependent optical interference fringe pattern and, responsive thereto, providing an electrical signal output; and
   processing means for receiving said electrical signal output from said detector means and processing the same to provide therefrom an accurate output indicative of the index of refraction of said ambient atmosphere.

2. The system of claim 1 wherein said light conducting means includes at least cylindrical lens means to provide concentrated diverging light from a frequency-stabilized light source.

3. The system of claim 1 wherein said refractometer means includes Fabry-Perot etalon means.

4. The system of claim 1 wherein said enabling means causes scanning of the concentrated light from said light conducting means at different angles with respect to said refractometer means to provide said refractivity-dependent interference fringe pattern.

5. The system of claim 1 wherein said enabling means causes said concentrated light to be nonparallel when received by said refractometer means, and wherein said enabling means causes imaging of said refractivity-dependent interference fringe pattern onto said detector means.

6. The system of claim 5 wherein said enabling means includes a concave mirror for focusing said refractivity-dependent interference fringe pattern in the far field onto said detector means.

7. The system of claim 1 wherein said detector means includes a multi-element detector.

8. The system of claim 7 wherein said multi-element detector is formed as one of a charge-coupled device array and a diode array.

9. The system of claim 1 wherein said processing means includes a microprocessor having a fringe-fitting algorithm.

10. The system of claim 1 wherein said ambient atmosphere is air.

11. The system of claim 1 wherein said system is a noninvasive system for enhancing the accuracy of a measuring apparatus exposed to said ambient atmosphere.

12. A measuring unit utilizing in-situ determined refractivity of an ambient atmosphere to provide a highly accurate quantity measurement in said ambient atmosphere, said unit comprising:
   measuring means exposed to said ambient atmosphere providing an electrical signal output indicative of a predetermined quantity to be measured;
   light conducting means adapted to provide light from a stabilized light source;
   refractometer means exposed to said ambient atmosphere the fractivity of which is to be determined, said refractometer means, upon receipt of said light from said light conducting means, providing an optical interference fringe pattern having a dependence upon the refractivity of said ambient atmosphere;
   optical imaging system for receiving said interference fringe pattern from said refractometer means and providing an output indicative of the far field of said pattern;
   multi-element detector means for receiving said output from said optical imaging means and, responsive thereto, providing an electrical signal output indicative of said far field fringe patter; and
   processing means for receiving said electrical signal outputs from said measuring means and said multi-element detector means, said processing means determining in-situ the index of refraction of said ambient atmosphere and, responsive thereto, correcting said quantity measurement to thereby provide a highly accurate quantity measurement output.

13. The unit of claim 12 wherein said measuring means includes interferometer means connected with said light conducting means, and second optical imaging means and multi-element detector means to provide said quantity indicative measurement.

14. The unit of claim 12 wherein said refractometer means is a Fabry-Perot etalon, and wherein said light means is an HeNe laser.

15. The unit of claim 12 wherein said processing means is a microprocessor having a fringe-fitting algorithm.

16. A method for providing accurate in-situ determination of the refractivity of an ambient atmosphere, said method comprising:
   providing a concentrated source of light at different angles;
   utilizing said concentrated source of light at different angles in an ambient atmosphere to form an optical interference fringe pattern having a dependence upon the refractivity of said ambient atmosphere with said refractivity-dependent optical interference fringe pattern being measurable as modulation of the input angular distribution from said concentrated source of light;
   detecting the phase of said measurable refractivity-dependent optical interference fringe pattern and providing an electrical signal output indicative thereof; and
   processing the electrical signal output to determine the index of refraction of said ambient atmosphere.

17. The method of claim 16 wherein said method includes sequentially scanning the source of light at different angles of incidence to enable said refractivity-dependent optical interference fringe pattern to be measured.

18. The method of claim 16 wherein said method includes imaging said refractivity-dependent optical interference fringe pattern in the far field to enable said refractivity-dependent optical interference fringe pattern to be measured.

19. The method of claim 18 wherein said method includes providing a Fabry-Perot etalon to form said interference fringe pattern, providing an output mirror with substantially flat surfaces at said Fabry-Perot etalon, and providing a concave focussing mirror to image said pattern in the far field.

20. The method of claim 18 wherein said method includes providing a Fabry-Perot etalon to form said interference fringe pattern, providing a lens surface as the output at said Fabry-Perot etalon, and providing a mirror having a substantially flat reflecting surface to image said pattern in the far field.

21. The method of claim 16 wherein said method includes providing a multi-element detecting means to detect the far field pattern.

22. The method of claim 16 wherein said method includes utilizing a fringe-fitting algorithm to determine the index of refraction.

23. The method of claim 22 wherein said fringe-fitting algorithm includes acquiring data by digitizing the received fringe patterns, finding peaks with respect to the data by convoluting with a step/anti-step function and looking for zero crossings, nonlinearly least squares fitting the data for parameters excess order and symmetry center, using the center to linearize the data and transforming to a new axis having peaks appearing substantially evenly spaced and symmetric, finding peaks for the data transformed to a new axis by convoluting with a step/anti-step function and looking for zero crossings, and linearly least square fitting the data for excess order on left and right of center and averaging.

24. The method of claim 16 wherein said method is utilized in conjunction with a measuring apparatus providing an output indicative of a predetermined quantity being measured, and wherein said determined index of refraction is used to enhance the accuracy of said measured quantity.

25. The method of claim 24 wherein said quantity being measured is distance, and wherein uncertainty in said distance measured is reduced.

* * * * *